United States Patent [19]

Schriewer et al.

[11] Patent Number: 4,956,465
[45] Date of Patent: Sep. 11, 1990

[54] QUINOLONE- AND 1,8-NAPHTHYRIDIN-4-ONE-CARBOXYLIC ACIDS WHICH ARE C-BONDED IN THE 7-POSITION

[75] Inventors: Michael Schriewer; Klaus Grohe, both of Odenthal; Uwe Petersen, Leverkusen, all of Fed. Rep. of Germany

[73] Assignee: Bayer Aktiengesellschaft, Leverkusen, Fed. Rep. of Germany

[21] Appl. No.: 252,631

[22] Filed: Oct. 3, 1988

[30] Foreign Application Priority Data

Oct. 9, 1987 [DE] Fed. Rep. of Germany ....... 3734161
Apr. 2, 1988 [DE] Fed. Rep. of Germany ....... 3811341

[51] Int. Cl.$^5$ .......................................... C07D 215/56
[52] U.S. Cl. .................................. 546/156; 546/123
[58] Field of Search ......................................... 546/156

[56] References Cited

U.S. PATENT DOCUMENTS

| | | | |
|---|---|---|---|
| 2,519,411 | 8/1950 | Surrey | 546/177 |
| 3,472,859 | 10/1969 | Lesher | 546/156 |
| 3,753,993 | 8/1973 | Lesher et al. | 546/156 |
| 3,960,868 | 6/1976 | Ferrini et al. | 546/156 |
| 4,623,650 | 11/1986 | Gilligan | 546/156 |
| 4,760,057 | 7/1988 | Alexander | 514/314 |
| 4,762,844 | 8/1988 | Grohe et al. | 546/156 |
| 4,764,518 | 8/1988 | Larvelle | 514/314 |
| 4,804,760 | 2/1989 | Schriewer et al. | 546/156 |
| 4,880,814 | 11/1989 | Chu et al. | 546/156 |

FOREIGN PATENT DOCUMENTS 0181588 5/1986 European Pat. Off. .

OTHER PUBLICATIONS

Chemical Abstracts, vol. 108, 1988, p. 735.

Primary Examiner—Donald G. Daus
Attorney, Agent, or Firm—Sprung, Horn, Kramer & Woods

[57] ABSTRACT

As novel intermediates for antibacterials, the quinolone- and 1,8-naphthyridine-4-one-carboxylic acids which are C-bonded in the 7-position of the formula

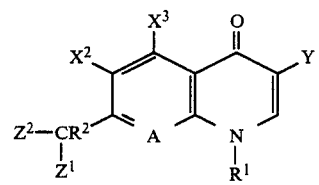

in which Y represents a carboxyl group, a nitrile group, an ester group —COOR$^3$, or an acid amide group —CONR$^4$R$^5$, where R$^3$ stands for C$_1$–C$_4$-alkyl, X$^2$ stands for hydrogen, nitro, alkyl having 1 to 3 carbon atoms and halogen, in particular R$^1$ can be alkyl having 1–4 carbon atoms, vinyl, halogenoalkyl, hydroxyalkyl, cycloalkyl having 1–6 carbon atoms or optionally substituted phenyl, R$^2$ stands for hydrogen, alkyl having 1–3 carbon atoms which is optionally substituted by halogen, alkoxy having 1–2 carbon atoms or nitro, phenyl and for a radical

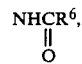

and Z$^1$ and Z$^2$ can each be hydrogen or various organic radicals or together form a ring, and salts and esters thereof.

5 Claims, No Drawings

QUINOLONE- AND 1,8-NAPHTHYRIDIN-4-ONE-CARBOXYLIC ACIDS WHICH ARE C-BONDED IN THE 7-POSITION

The invention relates to new 4-quinolone-3-carboxylic acid derivatives and naphthyridin-4-one carboxylic acid derivatives which are carbon-substituted in the 7-position, a process for their preparation and their use as intermediates for the preparation of highly active antibacterial quinolonecarboxylic acids and 1,8-naphthyridin-4-onecarboxylic acids.

By way of example, reference may be made to the use as intermediates for the preparation of antibacterially active alkyl quinolonecarboxylic acids, which are described in European Patent Application 0,181,588, which corresponds to U.S. Pat. No. 4,672,844.

Such compounds are considerably more easily available than previously by the process according to the invention. This relates in particular also to derivatives having substituted alkyl radicals.

The invention relates to compounds of the formula I and a process for the preparation of compounds of the formula I

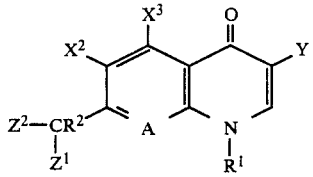

in which

Y represents a carboxyl group, a nitrile group, an ester group —COOR$^3$, or an acid amide group —CONR$^4$R$^5$, where R$^3$ stands for C$_1$–C$_4$-alkyl, R$^4$ and R$^5$ stand for hydrogen or C$_1$–C$_4$-alkyl, and R$^5$ additionally can be optionally substituted phenyl, X$^2$ stands for hydrogen, nitro, alkyl having 1 to 3 carbon atoms and halogen, in particular chlorine, bromine or fluorine, X$^3$ can be hydrogen, halogen, in particular chlorine, bromine or fluorine, or methyl, A stands for nitrogen or a radical C—X$^4$, where X$^4$ can be hydrogen, halogen, in particular chlorine, bromine or fluorine, nitro, cyano or methyl, R$^1$ can be alkyl having 1–4 carbon atoms, vinyl, halogenoalkyl, hydroxyalkyl, cycloalkyl having 1–6 carbon atoms or optionally substituted phenyl, R$^2$ stands for hydrogen, alkyl having 1–3 carbon atoms which is optionally substituted by halogen, alkoxy having 1–2 carbon atoms or nitro, phenyl and for a radical

NHCR$^6$, where

R$^6$ denotes hydrogen, alkyl having 1–3 carbon atoms and phenyl.

Z$^1$ and Z$^2$ can be identical or different and can stand for hydrogen, alkyl having 1–3 carbon atoms, optionally substituted phenyl, pyridyl, alkoxycarbonyl having 1–4 carbon atoms in the alcohol part, cyano, isocyano, nitro, formyl, and furthermore for COR$^7$, SOR$^8$, SO$_2$R$^9$, SO$_2$OR$^{10}$ and SO$_2$NR$^{11}$R$^{12}$ radicals, with the proviso that Z$^1$ and Z$^2$ are not simultaneously hydrogen or alkyl. In addition, Z$^1$ and Z$^2$, with the carbon atom to which they are bonded, can form a 5- or 6-membered ring which can contain the groups

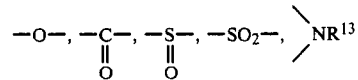

as ring members and which can be monosubstituted or disubstituted on the carbon atoms by C$_1$–C$_3$-alkyl, phenyl, halogen, nitro, cyano or alkoxycarbonyl having 1–3 carbon atoms in the alcohol part, where R$^7$, R$^8$, R$^9$ and R$^{10}$ stand for alkyl having 1–3 carbon atoms or optionally substituted phenyl, R$^{11}$ and R$^{12}$ can be identical or different and stand for hydrogen, alkyl having 1–3 carbon atoms or optionally substituted phenyl, and R$^{13}$ stands for C$_1$–C$_3$-alkyl or phenyl.

The compounds are suitable as intermediates for antibacterially active quinolonecarboxylic acids and naphthyridonecarboxylic acids.

Particularly preferred compounds of the formula I are those in which

Y stands for cyano or a carboxylic ester group —COOR$^3$, where R$^3$ stands for C$_1$–C$_4$-alkyl, X$^2$ and X$^3$ stand for hydrogen and halogen, in particular chlorine or fluorine, A stands for nitrogen or a radical C—X$^4$, where X$^4$ can be hydrogen, halogen, in particular chlorine or fluorine, nitro or cyano, R$^1$ denotes ethyl, vinyl, cyclopropyl or optionally substituted phenyl, R$^2$ stands for hydrogen or C$_1$–C$_3$-alkyl, and Z$^1$ and Z$^2$ can be identical or different and can stand for optionally substituted phenyl, pyridyl, alkoxycarbonyl having 1–4 carbon atoms in the alcohol part, cyano, isocyano, nitro, formyl or the radical COR$^7$, where R$^7$ stands for alkyl having 1–3 carbon atoms.

It has been found that the compounds of the formula I according to the invention are obtained when compounds of the formula II

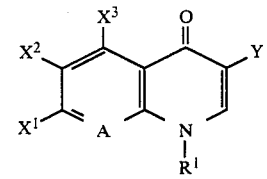

in which

Y, A, X$^2$ and X$^3$ have the abovementioned meaning and X$^1$ stands for halogen, preferably for chlorine and fluorine, are reacted with compounds of the formula III

in which R$^2$, Z$^1$ and Z$^2$ have the abovementioned meaning, in the presence of a base.

If, for example, ethyl 1-cyclopropyl-6,7,8-trifluoro-1,4-dihydro-4-oxo-3-quinoline-carboxylate and diethyl malonate are used as starting materials, then the course of the reaction can be represented by the following equation:

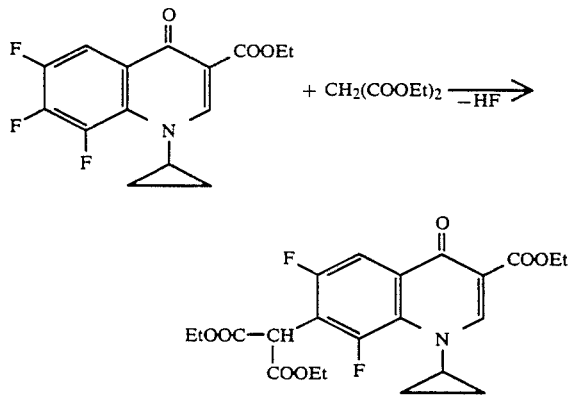

The quinolone carboxylic acid derivatives of the formula II required as starting materials according to this equation are known or can be prepared by known methods. Examples which may be mentioned are: ethyl 1-cyclopropyl-6,7,8-trifluoro-1,4-dihydro-4-oxo-3-quinoline-carboxylate, ethyl 1-cyclopropyl-6,7-difluoro-1,4-dihydro-4-oxo-3-quinoline-carboxylate, ethyl 7-chloro-1-cyclopropyl-6-fluoro-1,4-dihydro-4-oxo-3-quinoline-carboxylate, ethyl 6,8-dichloro-1-cyclopropyl-7-fluoro-1,4-dihydro-4-oxo-3-quinoline-carboxylate, ethyl 8-chloro-1-cyclopropyl-6,7-difluoro-1,4-dihydro-4-oxo-3-quinoline-carboxylate, ethyl 6-chloro-1-cyclopropyl-7,8-difluoro-1,4-dihydro-4-oxo-3-quinoline-carboxylate, ethyl 7-chloro-1-cyclopropyl-6-fluoro-1,4-dihydro-4-oxo-1,8-naphthyridine-3-carboxylate, ethyl 6,7-dichloro-1-cyclopropyl-1,4-dihydro-4-oxo-1,8-naphthyridine-3-carboxylate, ethyl 1-cyclopropyl-6,7,8-trifluoro-1,4-dihydro-4-oxo-3-quinoline-carboxylate, ethyl 7-chloro-6-fluoro-1,4-dihydro-4-oxo-1-phenyl-1,8-naphthyridine-3-carboxylate, ethyl 7-chloro-6-fluoro-1-(4-fluorophenyl)-1,4-dihydro-4-oxo-1,8-naphthyridine-3-carboxylate, methyl 7-chloro-1-ethyl-6-fluoro-1,4-dihydro-4-oxo-3-quinoline-carboxylate, 7-chloro-1-cyclopropyl-6-fluoro-1,4-oxo-3-quinoline-carbonitrile, 7-chloro-1-cyclopropyl-1,4-dihydro-4-oxo-3-quinolinecarbonitrile, ethyl 7-chloro-1-cyclopropyl-1,4-dihydro-6-nitro-4-oxo-3-quinoline-carboxylate, ethyl 6,7-dichloro-1-cyclopropyl-1,4-dihydro-4-oxo-3-quinoline-carboxylate, ethyl 1-cyclopropyl-7-chloro-6-fluoro-1,4-dihydro-8-nitro-4-oxo-3-quinoline-carboxylate, ethyl 6,7-difluoro-1-ethyl-1,4-dihydro-4-oxo-3-quinoline-carboxylate, methyl 7-chloro-1-ethyl-6-fluoro-1,4-dihydro-4-oxo-3-quinoline-carboxylate, ethyl 6,7-difluoro-1-(2-fluoroethyl)-1,4-dihydro-4-oxo-3-quinoline-carboxylate, ethyl 7-chloro-6-fluoro-1,4-dihydro-1-methoxy-4-oxo-3-quinoline-carboxylate, ethyl 6,7-difluoro-1,4-dihydro-4-oxo-1-phenyl-3-quinoline-carboxylate, ethyl 7-chloro-6-fluoro-1,4-dihydro-8-nitro-4-oxo-1-phenyl-3-quinoline-carboxylate, ethyl 7-chloro-6-fluoro-1-(4-fluorophenyl)-1,4-dihydro-8-nitro-4-oxo-3-quinoline-carboxylate, ethyl 6,7-difluoro-1-(4-fluorophenyl)-1,4-dihydro-8-methyl-4-oxo-3-quinoline-carboxylate, ethyl 6-chloro-7-fluoro-1-(4-fluorophenyl)-1,4-dihydro-4-oxo-3-quinoline-carboxylate, ethyl 6-chloro-7-fluoro-1-(2,4-difluorophenyl)-1,4-dihydro-4-oxo-3-quinoline-carboxylate, ethyl 6,7,8-trifluoro-1-(4-fluorophenyl)-1,4-dihydro-4-oxo-3-quinoline-carboxylate, ethyl 6,7,8-trifluoro-1-(2,4-difluorophenyl)-1,4-dihydro-4-oxo-3-quinoline-carboxylate, ethyl 6,7,8-trifluoro-1,4-dihydro-4-oxo-1-phenyl-3-quinoline-carboxylate, ethyl 7-chloro-1-ethyl-6-fluoro-1,4-dihydro-4-oxo-1,8-naphthyridine-3-carboxylate and ethyl 6,7-difluoro-1,4-dihydro-4-oxo-1-vinyl-3-quinoline-carboxylate.

The compounds of the formula III required as starting materials are known. Examples which may be mentioned are: diethyl malonate, dimethyl malonate, malononitrile, methyl cyanoacetate, ethyl cyanoacetate, t-butyl cyanoacetate, benzyl cyanide, 4-nitrobenzyl cyanide, 2-nitrobenzyl cyanide, 2-pyridylacetonitrile, 3-pyridylacetonitrile, ethyl acetoacetate, benzyl methyl sulphoxide, benzyl methyl sulphone, 2-benzylpyridine, 4-benzylpyridine, ethyl isocyanoacetate and benzyl isocyanate.

The reaction of II with III is preferably performed in a diluent such as dimethylformamide, dimethyl sulphoxide, hexamethylphosphoric acid triamide, sulpholane, dioxane, tetrahydrofuran or pyridine. Mixtures of these diluents can likewise be used.

Bases which can be employed are: sodium amide, sodium hydride, potassium t-butoxide, n-butyllithium and phenyllithium.

The reaction temperatures can be varied within a relatively wide range. In general, the reaction is carried out at between about 20° and 200° C., preferably between 80° and 180° C.

The reaction can be carried out at atmospheric pressure, but also at elevated pressure. In general, the reaction is carried out at pressures between about 1 and about 100 bar, preferably between 1 and 10 bar.

When carrying out the process according to the invention, 1 to 5 moles, preferably 1 to 3 moles, of the compound III are employed per mole of carboxylic acid derivative (II). One mole of a base is employed per mole of the compound III, it being advantageous to employ an excess of 10%.

The following derivatives may be mentioned in addition to the compounds mentioned in the examples: 7-(cyano-ethoxycarbonyl-methyl)-1-cyclopropyl-6,8-difluoro-1,4-dihydro-4-oxo-3-quinolinecarbonitrile, 7-(cyano-methoxycarbonyl-methyl)-1-cyclopropyl-6,8-difluoro-1,4-dihydro-4-oxo-3-quinolinecarbonitrile, 1-cyclopropyl-7-(bis-ethoxycarbonyl-methyl)-6,8-difluoro-1,4-dihydro-4-oxo-3-quinolinecarbonitrile, 7-(cyanophenyl-methyl)-1-cyclopropyl-6,8-difluoro-1,4-dihydro-4-oxo-3-quinolinecarbonitrile, 1-cyclopropyl-6,8-difluoro-1,4-dihydro-7-(methylsulphonyl-phenyl-methyl)-4-oxo-3-quinolinecarbonitrile, 7-(3-acetylacetonyl)-1-cyclopropyl-6,8-difluoro-1,4-dihydro-4-oxo-3-quinolinecarbonitrile, methyl 7-(cyano-ethoxycarbonyl-methyl)-1-cyclopropyl-6,8-difluoro-1,4-dihydro-4-oxo-3-quinoline-carboxylate, methyl 7-(cyano-methoxycarbonyl-methyl)-1-cyclopropyl-6,8-difluoro-1,4-dihydro-4-oxo-3-quinoline-carboxylate, methyl 1-cyclopropyl-7-(bis-ethoxycarbonylmethyl)-6,8-difluoro-1,4-dihydro-4-oxo-3-quinoline-carboxylate, methyl 7-(cyano-phenyl-methyl)-1-cyclopropyl-6,8-difluoro-1,4-dihydro-4-oxo-3-quinoline-carboxylate, methyl 1-cyclopropyl-6,8-difluoro-1,4-dihydro-7-(methylsulphonyl-phenyl-methyl)-4-oxo-3-quinoline-carboxylate, methyl 7-(3-acetylacetonyl)-1-cyclopropyl-6,8-difluoro-1,4-dihydro-4-oxo-3-quinoline-carboxylate, ethyl 6-chloro-7-(cyano-ethoxycarbonylmethyl)-1- cyclopropyl-8-fluoro-1,4-dihydro-4-oxo-3-quinoline-carboxylate, ethyl 6-chloro-7-(cyano-methoxycarbonyl-methyl)-1-cyclopropyl-8-fluoro-1,4-dihydro-4-oxo-3-quinoline-carboxylate, ethyl 6-chloro-1-cyclopropyl-7-(bis-ethoxycarbonyl-methyl)-8-fluoro-1,4-dihydro-4-oxo-3-quinoline-carboxylate, ethyl 6-chloro-7-(cyano-phenyl-methyl)-1-cyclopropyl-8-fluoro-1,4-dihydro-4-oxo-3-quinoline-carboxylate, ethyl 6-chloro-1-cyclopropyl-8-fluoro-1,4-dihydro-7-(methylsulphonyl-phenyl-methyl)-4-oxo-3-quinoline-carboxylate, ethyl 7-(3-acetylacetonyl)-6-chloro-1-cyclopropyl-8-fluoro-1,4-dihydro-4-oxo-3-quinoline-carboxylate, ethyl 8-chloro-7-(cyanoethoxycarbonyl-methyl)-1-cyclopropyl-6-fluoro-1,4-dihydro-4-oxo-3-quinoline-carboxylate, ethyl 8-chloro-7-(cyano-methoxycarbonyl-methyl)-1-cyclopropyl-6-fluoro-1,4-dihydro-4-oxo-3-quinoline-carboxylate, ethyl 8-chloro-1-cyclopropyl-7-(bis-ethoxycarbonyl-methyl)-6-fluoro-1,4-dihydro-4-oxo-3-quinoline-carboxylate, ethyl 8-chloro-7-(cyano-phenyl-methyl)-1-cyclopropyl-6-fluoro-1,4-dihydro-4-oxo-3-quinoline-carboxylate, ethyl 8-chloro-1-cyclopropyl-6-fluoro-1,4-dihydro-7-(methylsulphonyl-phenyl-methyl)-4-oxo-3-quinoline-carboxylate, ethyl 7-(3-acetylacetonyl)-8-chloro-1-cyclopropyl-6-fluoro-1,4-dihydro-4-oxo-3-quinoline-carboxylate, ethyl 7-(cyano-methoxycarbonyl-methyl)-6,8-difluoro-1,4-dihydro-4-oxo-1-phenyl-3-quinoline-carboxylate, ethyl 7-(bis-ethoxycarbonyl-methyl)-6,8-difluoro-1,4-dihydro-4-oxo-1-phenyl-3-quinoline-carboxylate, ethyl 7-(cyano-phenyl-methyl)-6,8-difluoro-1,4-dihydro-4-oxo-1-phenyl-3-quinoline-carboxylate, ethyl 6,8-difluoro-1,4-dihydro-7(methylsulphonyl-phenyl-methyl)-4-oxo-1-phenyl-3-quinoline-carboxylate, ethyl 7-(3-acetylacetonyl)-6,8-difluoro-1,4-dihydro-4-oxo-1-phenyl-3-quinoline-carboxylate, ethyl 7-(cyano-ethoxycarbonyl-methyl)-6,8-difluoro-1,4-dihydro-4-oxo-1-vinyl-3-quinoline-carboxylate, ethyl 7-(cyano-methoxycarbonyl-methyl)-6,8-difluoro-1,4-dihydro-4-oxo-1-vinyl-3-quinoline-carboxylate, ethyl 7-(bis-ethoxycarbonyl-methyl)-6,8-difluoro-1,4-dihydro-4-oxo-1-vinyl-3-quinoline-carboxylate, ethyl 7-(cyano-phenyl-methyl)-6,8-difluoro-1,4-dihydro-4-oxo-1-vinyl-3-quinoline-carboxylate, ethyl 6,8-difluoro-1,4-dihydro-7-(methylsulphonyl-phenyl-methyl)-4-oxo-1-vinyl-3-quinoline-carboxylate, ethyl 7-(3-acetylacetonyl)-6,8-difluoro-1,4-dihydro-4-oxo-1-vinyl-3-quinoline-carboxylate, ethyl 7-(cyano-ethoxycarbonyl-methyl)-1-ethyl-6,8-difluoro-1,4-dihydro-4-oxo-3-quinoline-carboxylate, ethyl 7-(cyano-methoxycarbonyl-methyl)-1-ethyl-6,8-difluoro-1,4-dihydro-4-oxo-3-quinoline-carboxylate, ethyl 7-(bis-ethoxycarbonyl-methyl)-1-ethyl-6,8-difluoro-1,4-dihydro-4-oxo-3-quinoline-carboxylate, ethyl 7-(cyano-phenyl-methyl)-1-ethyl-6,8-difluoro-1,4-dihydro-4-oxo-3-quinoline-carboxylate, ethyl 1-ethyl-6,8-difluoro-1,4-dihydro-7-(methylsulphonyl-phenyl-methyl)-4-oxo-3-quinoline-carboxylate, ethyl 7-(3-acetylacetonyl)-1-ethyl-6,8-difluoro-1,4-dihydro-4-oxo-3-quinoline-carboxylate, ethyl 7-(cyano-ethoxycarbonyl-methyl)-1-cyclopropyl-6-fluoro-1,4-dihydro-4-oxo-1,8-naphthyridine-3-carboxylate, ethyl 7-(cyano-methoxycarbonyl-methyl)-1-cyclopropyl-6-fluoro-1,4-dihydro-4-oxo-1,8-naphthyridine-3-carboxylate, ethyl 1-cyclopropyl-7-(bis-ethoxycarbonyl-methyl)-6-fluoro-1,4-dihydro-4-oxo-1,8-naphthyridine-3-carboxylate, ethyl 7-(cyano-phenyl-methyl)-1-cyclopropyl-6-fluoro-1,4-dihydro-4-oxo-1,8-naphthyridine-3-carboxylate, ethyl 1-cyclopropyl-6-fluoro-1,4-dihydro-7-(methylsulphonyl-phenyl-methyl)-4-oxo-1,8-naphthyridine-3-carboxylate, ethyl 7-(3-acetylacetonyl)-1-cyclopropyl-6-fluoro-1,4-dihydro-4-oxo-1,8-naphthyridine-3-carboxylate, ethyl 1-cyclopropyl-6,8-difluoro-1,4-dihydro-7-(2,2-dimethyl-1,3-dioxane-4,6-dion-5-yl)-4-oxo-3-quinoline-carboxylate, ethyl 1-cyclopropyl-6-fluoro-1,4-dihydro-7-(2,2-dimethyl-1,3-dioxane-4,6-dion-5-yl)-4-oxo-3-quinoline-carboxylate, ethyl 6-chloro-1-cyclopropyl-8-fluoro-1,4-dihydro-7-(2,2-dimethyl-1,3-dioxane-4,6-dion-5-yl)-4-oxo-3-quinoline-carboxylate, ethyl 6,8-difluoro-1,4-dihydro-7-(2,2-dimethyl-1,3-dioxane-4,6-dion-5-yl)-4-oxo-1-phenyl-3-quinoline-carboxylate, ethyl 1-cyclopropyl-6-fluoro-1,4-dihydro-7-(2,2-dimethyl-1,3-dioxane-4,6-dion-5-yl)-4-oxo-1,8-naphthyridine-3-carboxylate, ethyl 1-cyclopropyl-6,8-difluoro-1,4-dihydro-7-(1,3-dimethyl-hexahydropyrimidine-2,4,6-trion-5-yl)-4-oxo-3-quinoline-carboxylate, ethyl 1-cyclopropyl-6-fluoro-1,4-dihydro-7-(1,3-dimethyl-hexahydropyrimidine-2,4,6-trion-5-yl)-4-oxo-3-quinoline-carboxylate, 6-chloro-1-cyclopropyl-6-fluoro-1,4-dihydro-7-(1,3-dimethyl-hexahydropyrimidine-2,4,6-trion-5-yl)-4-oxo-3-quinoline-carboxylic acid, ethyl 6,8-difluoro-1,4-dihydro-7-(1,3-dimethyl-hexahydropyrimidine-2,4,6-trion-5-yl)-4-oxo-1-phenyl-3-quinoline-carboxylate and ethyl 1-cyclopropyl-6-fluoro-1,4-dihydro-7-(1,3-dimethyl-hexahydropyrimidine-2,4,6-trion-5-yl)-4-oxo-1,8-naphthyridine-3-carboxylate.

The following examples illustrate the invention:

EXAMPLE 1

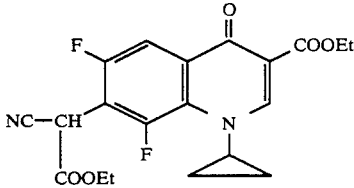

Ethyl 7-(cyano-ethoxycarbonyl-methyl)-1-cyclopropyl-6,8-difluoro-1,4-dihydro-4-oxo-3-quinoline-carboxylate 86.2 g of ethyl 1-cyclopropyl-6,7,8-trifluoro-1,4-dihydro-4-oxo-3-quinoline-carboxylate and 63.3 g of ethyl cyanoacetate are initially introduced into 1,000 ml of dioxane. 15.8 g of NaH are added in portions. The mixture is then heated to reflux for 4 hours. The completeness of the reaction is checked using thin-layer chromatography. After completion of the reaction, water is added dropwise. The mixture is then rendered acidic using dilute HCl and extracted using methylene chloride. The organic phase is dried and evaporated. The residue is recrystallized from isopropanol.

Yield: 86.5 g; melting point: 136°–37°.

| | $C_{20}H_{18}F_2N_2O_5$ | | | |
|---|---|---|---|---|
| calculated | C 59.4 | H 4.5 | N 7.0 | F 9.4 |
| found | 59.2 | 4.5 | 7.0 | 9.5 |
| | 59.0 | 4.0 | 6.9 | 9.5 |

EXAMPLE 2

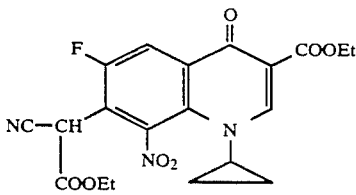

Ethyl
7-(cyano-ethoxycarbonyl-methyl)-1-cyclopropyl-6-fluoro-1,4-dihydro-8-nitro-4-oxo-3-quinoline-carboxylate 3.0 g of ethyl 7-chloro-1-cyclopropyl-6-fluoro-1,4-dihydro-8-nitro-4-oxo-3-quinoline-carboxylate and 1.92 g of ethyl cyanoacetate are initially introduced into 30 ml of dioxane. 1.91 g of potassium tert-butoxide are added in portions at room temperature. The mixture is stirred overnight and then heated to 50° for a further 4 hours. After cooling to room temperature, the mixture is diluted using ice-water and rendered acidic using HCl. The mixture is extracted using methylene chloride, and the organic phase is dried and concentrated. The residue is recrystallized from isopropanol.

Yield: 2.0 g; melting point: 135°–137° C.

| $C_{20}H_{18}F_2N_3O_7$ | | | |
|---|---|---|---|
| calculated | C 55.7 | H 4.2 | N 9.7 |
| found | 55.1 | 4.4 | 9.4 |
| | 55.3 | 4.6 | 9.2 |

EXAMPLE 3

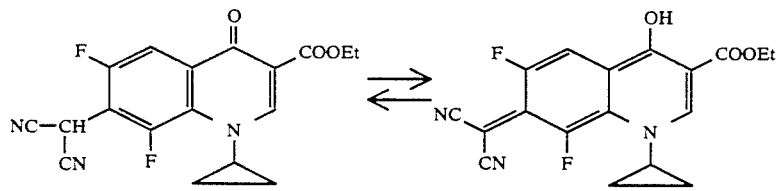

Ethyl
7-dicyanomethyl-1-cyclopropyl-6,8-difluoro-1,4-dihydro-4-oxo-3-quinoline-carboxylate 2.7 g of ethyl 1-cyclopropyl-6,7,8-trifluoro-1,4-dihydro-4-oxo-3-quinoline-carboxylate and 1.1 g of malononitrile are initially introduced into 30 ml of dioxane. 1.91 g of potassium tert-butoxide are added in portions. The mixture is warmed to 50° for 4 hours, cooled to room temperature, and acidified using HCl, and the red solid is isolated. It is recrystallized from glycol monomethyl ether.

Yield: 1.8 g; melting point: 208°–10° (dec.).

| $C_{18}H_{13}F_2N_3O_3$ | | | |
|---|---|---|---|
| calculated | C 60.5 | H 3.6 | N 11.8 | F 10.6 |
| found | 60.3 | 4.1 | 11.7 | 10.5 |
| | 60.4 | 3.9 | 11.9 | 10.4 |

According to the NMR and IR spectrum, the compound exists practically exclusively as the enol.

EXAMPLE 4

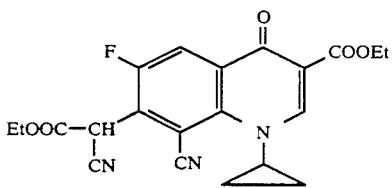

Ethyl
8-cyano-7-(cyano-ethoxycarbonyl-methyl-)-1-cyclopropyl-6-fluoro-1,4-dihydro-4-oxo-3-quinoline-carboxylate 2.8 g of ethyl 7-chloro-8-cyano-1-cyclopropyl-6-fluoro-1,4-dihydro-4-oxo-3-quinoline-carboxylate and 1.92 g of ethyl cyanoacetate are initially introduced into 30 ml of dioxane. 1.91 g of potassium tert-butoxide are metered in at room temperature. The mixture is stirred overnight and then ice-water is added. It is rendered acidic using HCl and extracted using methylene chloride. The organic phase is dried and concentrated. The residue is stirred once more with water and the solid is isolated.

Yield: 2.0 g; melting point 95°–115° (dec.).

Recrystallization from isopropanol yields a solid having the melting point 158°-59°.

EXAMPLE 5

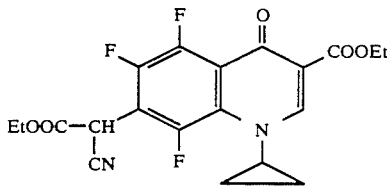

Ethyl
7-(cyano-ethoxycarbonyl-methyl)-1-cyclopropyl-5,6,8-trifluoro-1,4-dihydro-4-oxo-3-quinoline-carboxylate 6.6 of ethyl 1-cyclopropyl-5,6,7,8-tetrafluoro-1,4-dihydro-4-oxo-3-quinoline-carboxylate and 3.4 g of ethyl cyanoacetate are initially introduced into 100 ml of dioxane. 1.16 g of NaH are added in portions at room temperature. The mixture is heated to reflux for 6 hours and then diluted using water. After acidification using HCl, 9.4 g of the title compound can be isolated.

Melting point: 98°–100°.

The compound crystallizes with one mol of dioxane (detected by NMR)

EXAMPLE 6

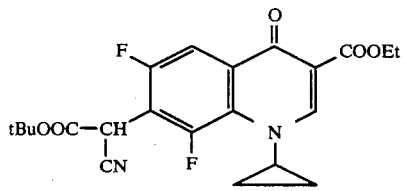

Ethyl 8-(t-butoxycarbonyl-cyanomethyl)-1-cyclopropyl-6,8-difluoro-1,4-dihydro-4-oxo-3-quinoline-carboxylate 3.1 g of ethyl 1-cyclopropyl-6,7,8-trifluoro-1,4-dihydro-4-oxo-3-quinoline-carboxylate and 2.1 g of t-butyl cyanoacetate are initially introduced into 30 ml of dioxane. 0.57 g of sodium hydride is added in portions. The mixture is boiled for 3 hours and then ice-water is added. After acidifying using HCl, the mixture is extracted with $CH_2Cl_2$. The organic phase is dried and concentrated. The residue is recrystallized from isopropanol.

Yield: 3.4 g; melting point: 143°-45°.

EXAMPLE 7

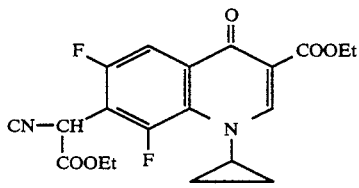

Ethyl 1-cyclopropyl-7-(ethoxycarbonyl-isocyanomethyl)-6,8-difluoro-1,4-dihydro-4-oxo-3-quinoline-carboxylate 2.7 g of ethyl 1-cyclopropyl-6,7,8-trifluoro-1,4-dihydro-4-oxo-3-quinoline-carboxylate and 1.92 g of ethyl isocyanoacetate are initially introduced into 30 ml of dioxane. 1.91 g of potassium tert-butoxide are added and the mixture is heated to reflux for 3 hours. 0.39 g of potassium tert-butoxide is then added once more and the mixture is once more boiled for 2 hours. It is then diluted using water, acidified using HCl and the solid is isolated. After separation on silica gel (eluant $CH_2Cl_2$/MeOH 95/5), 1.0 g of the title compound is obtained.

Melting point: 68°-71° (dec.).
IR 2149 cm$^{-1}$ (—N$^⊕$≡C$^⊖$).

EXAMPLE 8

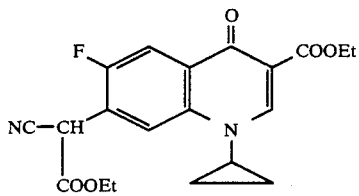

Ethyl 7-(cyano-ethoxycarbonyl-methyl)-1-cyclopropyl-6-fluoro-1,4-dihydro-4-oxo-3-quinoline-carboxylate 8.8 g of ethyl 1-cyclopropyl-6,7-difluoro-1,4-dihydro-4-oxo-3-quinoline-carboxylate and 5.1 g of ethyl cyanoacetate are initially introduced into 120 ml of dioxane. 1.74 g of NaH are added in portions. The mixture is then boiled for 3 hours, diluted with water and rendered acidic using HCl. It is extracted using methylene chloride. The organic phase is dried and concentrated. The residue is recrystallized from ethanol.

Yield: 9.2 g; melting point 152°-54°.

EXAMPLE 9

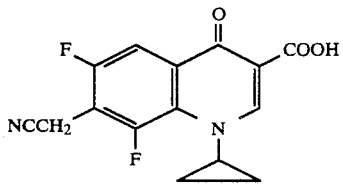

7-Cyanomethyl-1-cyclopropyl-6,8-difluoro-1,4-dihydro-4-oxo-3-quinolinecarboxylic acid 100 g of the compound from Example 1, 230 ml of acetic acid, 200 ml of water and 20 ml of sulphuric acid are boiled for 5 hours. After cooling to room temperature, water is added. The precipitated solid is isolated, washed with water and dried.

Yield: 71.5 g; melting point 219°-21°.

EXAMPLE 10

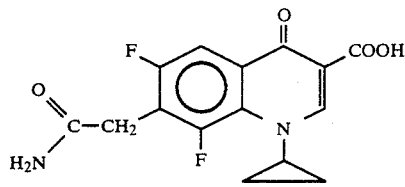

7-Carbamoylmethyl-1-cyclopropyl-6,8-difluoro-1,4-dihydro-4-oxo-3-quinolinecarboxylic acid 65 g of the compound from Example 9 are introduced into 600 ml of concentrated HCl. The mixture is stirred at room temperature until the educt is no longer detectable by thin-layer chromatography. The mixture is then poured onto ice and the precipitate is isolated. It is washed with plenty of water and dried in a vacuum drying cabinet. After recrystallization from a mixture of glycol monomethyl ether acetate and dimethylformamide, 46 g of the title compound are obtained.

Melting point: 280°-2° (dec.).

| | $C_{15}H_{12}F_2N_2O_4$ | | |
|---|---|---|---|
| calculated | C 55.9 | H 3.7 | N 8.7 |
| found | 56.2 | 3.9 | 8.6 |
| | 56.3 | 3.8 | 8.8 |

EXAMPLE 11

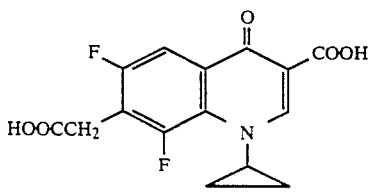

1-Cyclopropyl-6,8-difluoro-1,4-dihydro-7-hydroxycarbonylmethyl-4-oxo-3-quinolinecarboxylic acid 3.0 g of the compound from Example 10 are warmed to 90°–100° C. in 17 ml of 30% strength sulphuric acid. At this temperature, 6 ml of 2.5 molar sodium nitrite solution are added dropwise. The mixture is stirred for one hour more at 100° and then cooled. The precipitated solid is isolated, washed and dried.

Yield: 2.7 g; melting point 206°–7° (dec.).

| | $C_{15}H_{11}F_2NO_5$ | | |
|---|---|---|---|
| calculated | C 55.7 | H 3.4 | N 4.3 |
| found | 55.5 | 3.7 | 4.4 |
| | 55.2 | 3.4 | 4.3 |

EXAMPLE 12

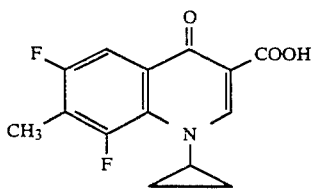

1-Cyclopropyl-6,8-difluoro-1,4-dihydro-7-methyl-4-oxo-3-quinolinecarboxylic acid 0.5 g of the compound from Example 11 is heated to 240° C. for one hour in 5 ml of diphenyl ether. The residue remaining after distilling off the solvent consists of 0.3 g of crude product of melting point 208°–10° C. Recrystallization from ethanol gives a melting point of 226°–28°.

This compound is described as very active as an antibacterial (EP 0,181,588).

EXAMPLE 13

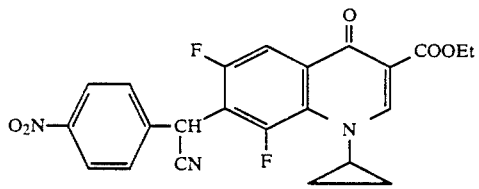

Ethyl 7-(cyano-4-nitrophenyl-methyl)-1-cyclopropyl-6,8-difluoro-1,4-dihydro-4-oxo-3-quinoline-carboxylate 3.3 g of 4-nitrobenzylnitrile are initially introduced into 24 ml of DMSO. 0.6 g of sodium hydride is then added. After gas evolution has ended, 4.0 g of ethyl 1-cyclopropyl-6,7,8-trifluoro-1,4-dihydro-4-oxo-3-quinoline-carboxylate are added. The reaction mixture is warmed to 100° C. for 6 hours. Water is then added and the mixture is rendered acidic using HCl. The solid is isolated, washed and dried. Separation on silica gel (eluant methylene chloride/methanol 96/4) yields 4.8 g of the title compound of melting point 85°–87° (dec.).

EXAMPLE 14

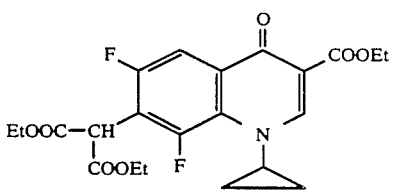

Ethyl 1-cyclopropyl-7-(bis-ethoxycarbonyl-methyl)-6,8-difluoro-1,4-dihydro-4-oxo-3-quinoline-carboxylate 2.0 g of the compound from Example 3 are initially introduced into 30 ml of ethanol. HCl gas is then introduced for 30 minutes. The mixture is heated to reflux for 3 hours and cooled, water is added and the mixture is extracted using methylene chloride. The organic phase is dried and evaporated. The residue is recrystallized from ethanol.

Yield: 1.2 g; melting point: 128°–29°.

EXAMPLE 15

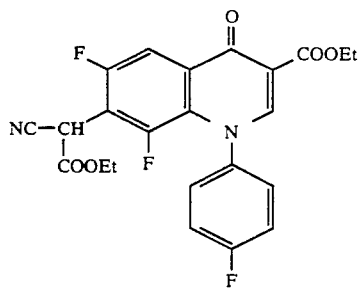

Ethyl 7-(cyano-ethoxycarbonyl-methyl)-6,8-difluoro-1-(4-fluorophenyl)-1,4-dihydro-4-oxo-3-quinoline-carboxylate 0.12 g of sodium hydride are initially introduced into 15 ml of dioxane. 0.51 g of ethyl cyanoacetate is added and the mixture is first stirred for one hour at room temperature. 1.1 g of ethyl 6,7,8-trifluoro-1-(4-fluorophenyl)-1,4-dihydro-4-oxo-3-quinoline-carboxylate are then added in portions. The mixture is boiled for 3 hours, diluted using water and acidified. It is extracted using methylene chloride.

The organic phase is dried and concentrated. The residue is recrystallized from ethanol.

Yield: 0.9 g; melting point: 172°–73°.

It will be appreciated that the instant specification and claims are set forth by way of illustration and not limitation, and that various modifications and changes may be made without departing from the spirit and scope of the present invention.

What is claimed is:

1. A quinolone carboxylic acid or 1,8-naphthyridin-4-onecarboxylic acid of the formula

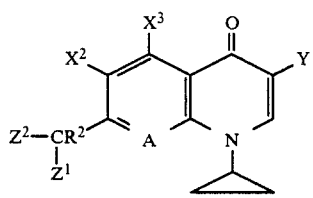

in which
Y is cyano or a —COO—$C_1$-$C_4$-alkyl group,
$X^2$ and $X^3$ each independently is hydrogen, chlorine or fluorine,
A is the radical C—$X^4$, where
$X^4$ is hydrogen, chlorine or fluorine
$R^2$ is hydrogen or $C_1$-$C_3$-alkyl, and
$Z^1$ is alkoxy-carbonyl having 1–4 carbon atoms in the alcohol part or hydrogen and $Z^2$ is cyano or alkoxycarbonyl having 1–4 carbon atoms in the alcohol part.

2. A compound according to claim 1, wherein such compound is ethyl 7-(cyano-ethoxycarbonyl-methyl)-1-cyclopropyl-6,8-difluoro-1,4-dihydro-4-oxo-3-quinoline-carboxylate of the formula

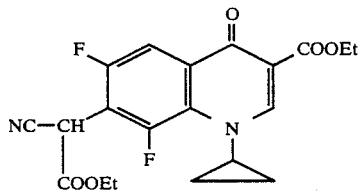

or a physiologically tolerable salt thereof.

3. A compound according to claim 1, wherein such compound is ethyl 7-(t-butoxycarbonyl-cyanomethyl)-1-cyclopropyl-6,8-difluoro-1,4-dihydro-4-oxo-3-quinoline-carboxylate of the formula

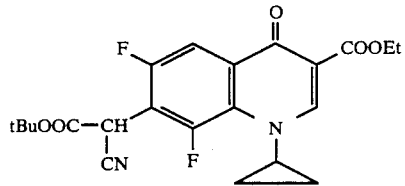

or a physiologically tolerable salt thereof.

4. A compound according to claim 1, wherein such compound is ethyl 7-(cyano-ethoxycarbonyl-methyl)-1-cyclopropyl-6-fluoro-1,4-dihydro-4-oxo-3-quinoline-carboxylate of the formula

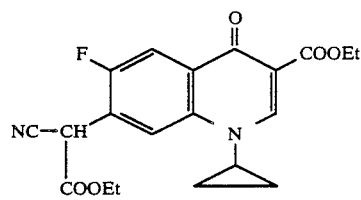

or a physiologically tolerable salt thereof.

5. A compound according to claim 1, wherein such compound is 7-cyanomethyl-1-cyclopropyl-6,8-difluoro-1,4-dihydro-4-oxo-3-quinolinecarboxylic acid of the formula

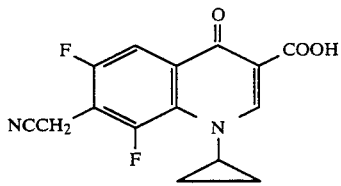

or a physiologically tolerable salt thereof.

* * * * *